United States Patent [19]

Hoffman et al.

[11] 4,056,541

[45] Nov. 1, 1977

[54] KETOLACTONES

[75] Inventors: Werner Hoffman, Neuhofen; Norbert Mueller, Mutterstadt; Karl von Fraunberg, Bobenheim, all of Germany

[73] Assignee: BASF Aktiengesellschaft, Ludwigshafen, Germany

[21] Appl. No.: 662,579

[22] Filed: Mar. 1, 1976

[30] Foreign Application Priority Data

Mar. 15, 1975 Germany .............................. 2511410

[51] Int. Cl.$^2$ ........................................... C07D 313/00
[52] U.S. Cl. ..................................... 260/343; 252/522
[58] Field of Search ......................................... 260/343

[56] References Cited

PUBLICATIONS

House, Modern Synthetic Reactions, second edition 1972 p. 358.

March, Advanced Organic Chemistry: Reactions, Mechanisms, and Structures, 1968, pp. 871, 872, 896.

*Primary Examiner*—Bernard Helfin
*Assistant Examiner*—Jane T. Fan
*Attorney, Agent, or Firm*—Keil, Thompson & Shurtleff

[57] ABSTRACT

New macrocyclic ketolactones, especially 15-methyl- 15-ethyl- and 15,15-dimethyl-12-oxo-15-hydroxytetradecanecarboxylic acid lactone.

The new ketolactones have an intense and delicate woody musky odor and may be employed as scents and fixatives.

3 Claims, No Drawings

KETOLACTONES

The present invention relates to new unsubstituted or alkyl- or vinyl-substituted 12-keto-ω-hydroxycarboxylic acid lactones of 14 to 16 carbon atoms in the ring.

The new compounds are ketolactones of the general formula I

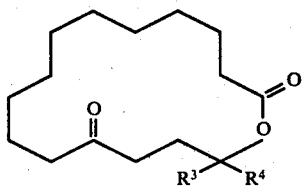

where $R^3$ and $R^4$ are $-CH_3$, $-C_2H_5$ or $-CH=CH_2$.

The new ketolactones have an intense and delicate woody musky odor which clings excellently and can therefore be employed as high quality scents and fixatives. They can be manufactured simply and economically from cyclododecanone, which is a readily accessible compound.

We have found a process for the manufacture of the new ketolactones of the general formula I, wherein compounds of the general formula II

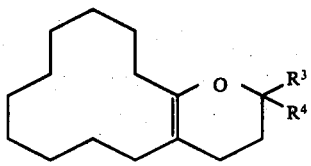

where $R^3$ and $R^4$ have the above meanings, are ozonolyzed and the ozonization products are then subjected to hydrolytic or reductive scission.

The compounds of the formula II required as starting materials may be manufactured in a simple manner, eg. from cyclododecanone-α-carboxylic acid esters.

For this purpose the cyclododecanone carboxylic acid esters may, eg., be converted to the compounds of the formula V by reaction with the allyl halides III or by a Carrol reaction with the alcohols IV. The compounds V can be cyclized either directly, or after prior hydration of the double bonds, to give the enol-ethers of the general formula II.

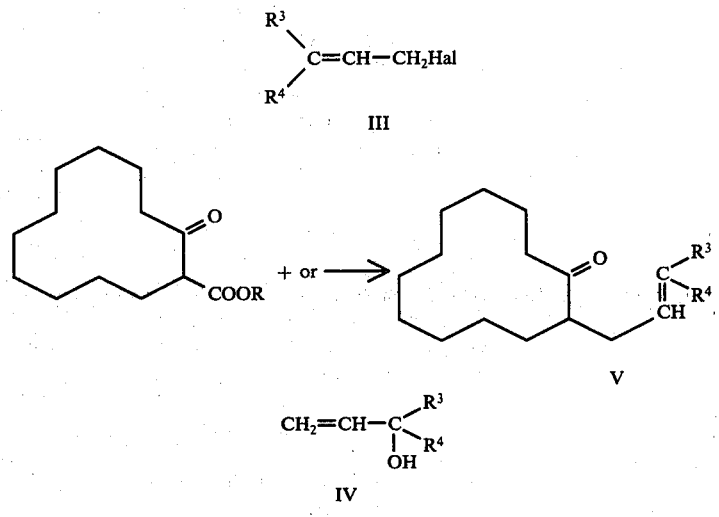

The ozonolysis is generally carried out by dissolving the compound of the general formula II in a conventional solvent for ozonolyses and passing into this solution, at the reaction temperature, sufficient of a stream of gas, consisting of $O_2$ and $O_3$ and containing a known amount of the latter, to introduce from about 1 to 3 moles, and preferably from 1.5 to 2 moles, of ozone into the reaction mixture per mole of the compound of the formula II.

Examples of solvents conventionally used for ozonolyses are pure or chlorinated hydrocarbons, eg. pentane, hexane, carbon tetrachloride, trichloroethane and methylene chloride, and ethyl acetate, ie. solvents which are inert under the reaction conditions, and also nucleophilic solvents, eg. methanol.

If inert solvents are used, ozonides are formed as intermediates, whilst if nucleophilic solvents are used, the reaction of the solvents with the primary ozonide results in the formation of hydroperoxides as intermediates (eg., methoxylated hydroperoxides are formed when methanol is used).

Both intermediates can be split hydrolytically or reductively, by conventional methods, to give the reaction products of the formula I. Of course, mixtures of inert solvents and nucleophilic solvents, such as mixtures of methanol and methylene chloride, may also be used. The solvents are generally used in amounts of from 10 to 100 moles, preferably about 50 moles, per mole of the compound of the formula II.

The ozonolysis reaction temperature is generally from $-50°$ to $+50°$ C and preferably from $-30°$ to $0°$ C.

If flammable solvents are used, the explosive limit of the mixture of solvent and $O_2$ must be borne in mind. For example, this is $+1.8°$ C for the mixture of $O_2$ and methanol.

The reaction time depends on the amount of $O_3$ provided by the ozonizer which is available. A high-output ozonizer is described, eg., by G. Wagner in J. prakt. Chem. (4), 13, 99 (1961).

The reaction mixture obtained from the ozonolysis is worked up by conventional methods, by hydrolytic or reductive scission, preferably by reductive scission.

Hydrolytic scission may be carried out with water at room temperature or, preferably with steam.

Reductive scission of the ozonolysis products may be carried out in various ways, eg. with trialkyl phosphites or triaryl phosphites, such as trimethyl phosphite, triethyl phosphite or triphenyl phosphite, with the systems NaI/thiosulfate, zinc/glacial acetic acid or zinc/50% strength acetic acid, by catalytic hydrogenation, eg. over Pd on calcium carbonate, or with metal hydrides, triphenylphosphine, sodium dithionite or $Na_2SO_3$.

Good yields, and at the same time particularly pure products, are obtained if the reductive scission is carried out with zinc and acetic acid of about 50% strength.

We shall therefore describe the working up of a mixture, obtained on ozonolysis of compounds of the formula II, with zinc and acetic acid, as an example of a reductive scission:

From 1 to 5 moles, preferably about 3 moles, per mole of the compound of the formula II, of zinc grit or zinc dust are added to the reaction mixture obtained from ozonolysis - after it has been flushed for several minutes with an inert gas (eg. nitrogen) to expel residual $O_3$ — at from $-50°$ to $0°$ C, and thereafter from about 3 to 4 moles, per mole of zinc, of acetic acid, preferably in the form of about 50% strength acetic acid, are added dropwise whilst continuing to cool the mixture intensively with brine or a mixture of acetone and solid carbon dioxide. The reduction manifests itself in an intense evolution of heat (the temperature rises approximately from $-25°$ to $+25°$ C), and is generally complete after from about 5 to 15 minutes. The reaction mixture is then stirred for some time, preferably from 1 to 2 hours, at room temperature, after which it is poured into, or filtered into, an approximately 4-fold to 5-fold amount of cold water. The mixture is then extracted with an inert solvent, eg. ether, chloroform or methylene chloride and the organic phase is washed neutral with $NaHCO_3$ solution, dried and concentrated under reduced pressure. The compound of the formula I can be purified by fractionating the crude product uner reduced pressure. Alternatively, the crude product can be purified by preparative layer chromatography, as described, eg., in Example 2c.

Regarding further possible ways of working up ozonolysis batches, reference may be made to Augustine "Oxidation," volume 1, pages 298-306, Marcel Dekker, Inc., New York, 1969.

By means of the process of the invention, the new 12-keto-ω-hydroxycarboxylic acid lactones of the formula I can be manufactured in a simple manner and in good yields. The new ketolactones have an intense and delicate musky odor and can therefore be used as high-quality scents and fixatives.

EXAMPLE 1 a. Manufacture of 2-[3-methyl-but-2-en-1-yl]-cyclododecanone

3-Methyl-but-1-en-3-ol is added dropwise to 208 g (0.82 mole) of cyclododecanone-2-carboxylic acid ethyl ester at 160° C until the boiling point at the top of a small column no longer drops below 85° C/750 mm Hg. The temperature of the batch is then slowly raised to 200° C and kept thereat until no further $CO_2$ is evolved. Fractional distillation of the reaction mixture gives 151 g of 2-[3-methyl-but-2-en-1-yl]-cyclododecanone of boiling point 132° - 135° C/0.01 mm Hg. This corresponds to a yield of 74% of theory.

b. Preparation of 14,14-dimethyl-13-oxa-1,12-didehydrobicyclo[10.4.0]-hexadecane 112 g of 2-[3-methyl-but-2-en-1-yl]-cyclododecanone are added dropwise in the course of 5 minutes to 300 ml of 2-nitropropane and 300 g of sulfuric acid at $-40°$ C and the reaction mixture is stirred for 5 minutes at $-40°$ C. After adding 500 ml of ice water, the phases are separated. The water phase is extracted by shaking three times with 100 ml of toluene. The combined organic phases are washed neutral with 5% strength sodium carbonate solution and concentrated. The crude product is fractionated through a small column. 90 g of 14,14-dimethyl-13-oxa-1,12-didehydro-bicyclo[10.4.0]-hexadecane of boiling point 139° - 142° C/0.1 mm Hg are obtained. This corresponds to a yield of 80% of theory.

c. Preparation of 15,15-dimethyl-12-oxo-15-hydroxytetradecanecarboxylic acid lactone 0.2 mole of ozone mixed with oxygen is bubbled, in the course of 2.5 hours, into a solution of 25 g (0.1 mole) of 14,14-dimethyl-13-oxa-1,12-didehydro-bicyclo[10.4.0]hexadecane in 300 ml of methanol whilst stirring vigorously at 0° C. (The amount of ozone provided by the ozonier per unit time was determined in a parallel circuit, from the $I_2$ formed in a KI solution buffered with HOAc.)

The reaction solution is cooled to $-50°$ C, 20 g (0.3 mole) of zinc are introduced, and 140 ml of 50% strength aqueous acetic acid are added dropwise. The temperature is allowed to rise to 25° C in the course of 1 hour. The reaction mixture is filtered into 1 l of water, the batch is extracted five times with 200 ml of $CH_2Cl_2$, the combined extracts are washed neutral with 200 ml of $NaHCO_3$ solution and dried over $Na_2SO_4$ and the solvent is evaporated under reduced pressure.

The residue consists of 28 g of pale yellow oil. The yield of 15,15-dimethyl-12-oxo-15-hydroxy-tetradecanecarboxylic acid lactone is 57%, based on 14,14-dimethyl-13-oxa-1,12-didehydro-bicyclo[10.4.0]hexadecane converted.

It is not possible to obtain a pure product by fractionating a small amount at boiling point 130° - 150° C/0.01 mm Hg. Pure ketolactone is obtained by preparative layer chromatgraphy, as described in Example 2c.

The structure is confined by the IR and NMR spectra and by analysis.

| | |
|---|---|
| $\delta = 1.32$ ppm (12 H,S) | S = singlet |
| $\delta = 1.43$ ppm ( 6 H,S) | T = triplet |
| $\delta = 1.64$ ppm ( 4 H,M) | M = multiplet |
| $\delta = 1.99$ ppm ( 2 H,T) | |
| $\delta = 2.22$ ppm ( 2 H,T) | |
| $\delta = 2.38$ ppm ( 2 H,T) | |
| $\delta = 2.53$ ppm ( 2 H,T) | |

Scent: a delicate musky odor with a woody undertone and great radiance.

EXAMPLE 2 a. Preparation of 2-[3-methyl-pent-2-en-1-yl]-cyclododecanone 100 g (1.0 mole) of 3-methyl-pent-1-en-3-ol are added dropwise to 127 g (0.5 mole) of cyclododecanone-2-carboxylic acid ethyl ester at 160° C, whilst stirring, the addition being controlled so that the boiling point at the top of a small column remains below 90° C/760 mm Hg. The reaction temperature is then gradually raised to 200° C and the batch is kept at this temperature until no further carbon dioxide is evolved. The residue is fractionated and gives 112 g of 2-[3-methyl-pent-2-en-1-yl]-cyclododecanone of boiling point 128° – 132° C/0.01 mm Hg. This corresponds to a yield of 85% of theory.

b. Preparation of 14-methyl-14-ethyl-13-oxa-1,12-didehydro-bicyclo[10.4.0]hexadecane 130 g of 2-[3-methyl-pent-2-en-1-yl]-cyclododecanone are added dropwise in the course of 5 minutes to 60 ml of 2-nitropropane and 60 g of sulfuric acid at −40° C and the reaction mixture is stirred for 5 minutes at −40° to −35° C. Working up the mixture as described in Example 1 b, and subsequently distilling the product, gives 10.8 g of 14-methyl-14-ethyl-13-oxa-1,12-didehydro-bicyclo[[10.4.0]hexadecane. This corresponds to a yield of 83% of theory.

c. Preparation of 15-methyl-15-ethyl-12-oxo-15-hydroxy-tetradecanecarboxylic acid lactone 0.04 mole of ozone is passed into a solution of 7 g (0.027 mole) of 14-methyl-14-ethyl-13-oxa-1,12-didehydro-bicyclo[10.14.0]hexadecane in 100 ml of methanol in the course of 54 minutes, at room temperature. On reduction, as described in Example 1c, with 3 g of zinc and 20 g of 50% strength acetic acid, and subsequent working up as described in Example 1c, 7 g of crude product are obtained. 3 g are purified on 3 SiO₂ plates (coating: 100 cm × 20 cm × 0.1 cm), which are developed twice in a 10:1 mixture of cyclohexane and ethyl acetate.

1.3 g of 15-methyl-15-ethyl-12-oxo-15-hydroxytetradecanecarboxylic acid lactone are obtained.

The IR and NMR spectra confirm the structure.

| | |
|---|---|
| $\delta$ = 0.88 ppm ( 3 H,T) | S = singlet |
| $\delta$ = 1.32 ppm (12 H,S) | T = triplet |
| $\delta$ = 1.38 ppm ( 3 H,S) | Q = quadruplet |
| $\delta$ = 1.64 ppm ( 4 H,M) | M = multiplet |
| $\delta$ = 1.92 ppm ( 1 H,T) | |
| $\delta$ = 1.95 ppm ( 1 H,T) | |
| $\delta$ = 2.11 ppm ( 2 H,Q) | $\delta$ = 2.38 ppm (2 H,T) Scent: delicate, |
| $\delta$ = 2.26 ppm ( 2 H,T) | $\delta$ = 2.50 ppm (2 H,T) musky. |

EXAMPLE 3

Preparation of 14-methyl-12-oxo-15-hydroxy-tetradecanecarboxylic acid lactone 0.3 mole of O₃ is passed into a solution of 47.2 g (0.2 mole) of 15-methyl-13-oxa-1,12-didehydro-bicyclo[10.4.0]hexadecane in 500 ml of methanol in the course of 1 hour and 50 minutes at from 0° to 5° C.

On reduction as described in Example 1c with 20 g of Zn and 140 ml of 50% strength acetic acid and subsequent working up with water and CH₂Cl₂ as described in example 1c, 47 g of crude product of boiling point 145° – 150° C/0.06 mm Hg are obtained. According to analysis by gas chromatography, the yield of 14-methyl-12-oxo-15-hydroxy-tetradecanecarboxylic acid lactone is 54.4% of theory.

The IR and NMR spectra of a sample purified as described in Example 2c by means of layer chromatography confirm the structure.

$\delta$ = 0.92 ppm (3 H,D)
$\delta$ = 1.25 ppm (12 H,S)
$\delta$ = 2.14 ppm (12 H,S)
$\delta$ = 3.85 ppm (1 H,D)
$\delta$ = 4.00 ppm (1 H,D)

Scent: delicate musky odor with a woody undertone.

We claim:

1. The ketolactones of the general formula I

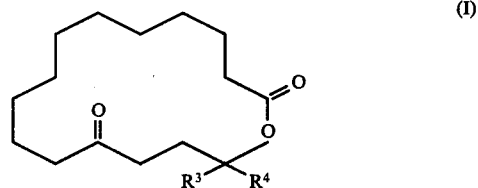

(I)

where R³ and R⁴ are —CH₃, —C₂H₅ or —CH= CH₂.

2. 15,15-Dimethyl-12-oxo-15-hydroxy-tetradecanecarboxylic acid lactone.

3. 15-Methyl-15-ethyl-1-oxo-15-hydroxy-tetradecannecarboxlic acid lactone.

* * * * *

UNITED STATES PATENT AND TRADEMARK OFFICE
CERTIFICATE OF CORRECTION

PATENT NO. : 4,056,541
DATED : November 1, 1977
INVENTOR(S) : Werner Hoffmann et al It is certified that error appears in the above-identified patent and that said Letters Patent are hereby corrected as shown below:

First page, left-hand column, first inventor should read --Werner Hoffmann--.

Column 6, second to last line, "1" should read --12--.

Signed and Sealed this

Eighth Day of August 1978

[SEAL]

Attest:

RUTH C. MASON
*Attesting Officer*

DONALD W. BANNER
*Commissioner of Patents and Trademarks*